(12) United States Patent  
Nabeshima et al.

(10) Patent No.: US 7,522,290 B2  
(45) Date of Patent: Apr. 21, 2009

(54) APPARATUS AND METHOD FOR INSPECTING SEMICONDUCTOR WAFER

(75) Inventors: Fumi Nabeshima, Hiratsuka (JP);  
Kazuya Togashi, Hiratsuka (JP)

(73) Assignee: Sumco Tech XIV Corporation, Nagasaki (JP)

( * ) Notice: Subject to any disclaimer, the term of this patent is extended or adjusted under 35 U.S.C. 154(b) by 42 days.

(21) Appl. No.: 11/569,249

(22) PCT Filed: Jun. 1, 2005

(86) PCT No.: PCT/JP2005/010051

§ 371 (c)(1),  
(2), (4) Date: Nov. 17, 2006

(87) PCT Pub. No.: WO2005/119226

PCT Pub. Date: Dec. 15, 2005

(65) Prior Publication Data

US 2007/0229815 A1    Oct. 4, 2007

(30) Foreign Application Priority Data

Jun. 2, 2004    (JP) .............................. 2004-164132

(51) Int. Cl.  
*G01B 11/02* (2006.01)

(52) U.S. Cl. ...................................... 356/516

(58) Field of Classification Search ................ 356/511, 356/516, 521  
See application file for complete search history.

(56) References Cited

U.S. PATENT DOCUMENTS

| | | | | |
|---|---|---|---|---|
| 3,796,495 A | * | 3/1974 | Laub | 356/489 |
| 6,943,898 B2 | * | 9/2005 | Libinson et al. | 356/516 |
| 7,019,840 B2 | * | 3/2006 | Wang et al. | 356/495 |
| 2004/0027577 A1 | * | 2/2004 | Sugiyama et al. | 356/498 |

FOREIGN PATENT DOCUMENTS

| | | |
|---|---|---|
| JP | H07-239212 A1 | 9/1995 |
| JP | 2000-162141 A1 | 6/2000 |
| JP | 2001-176943 A1 | 6/2001 |
| JP | 2003-004654 A1 | 1/2003 |

* cited by examiner

*Primary Examiner*—Michael A Lyons  
(74) *Attorney, Agent, or Firm*—Orion Consulting, Ltd.; Joseph Farrar

(57) ABSTRACT

A semiconductor wafer surface inspection apparatus detects LADs (Large Area Defects) which are flat and have low heights and differentiates them from particles. This inspection apparatus irradiates each point on the surface of a semiconductor wafer 200 with two parallel laser beams perpendicularly to the points while scanning the surface, and by measuring the phase difference between the two reflected beams, detects points 400 at which an upward inclination exists and points 402 at which a downward inclination exists on the surface of the wafer 200. Areas 404 in which pairs or sets of upward-inclination points 400 and downward-inclination points 402 exist within a prescribed range of mutual distances are inferred to be LADs.

3 Claims, 4 Drawing Sheets

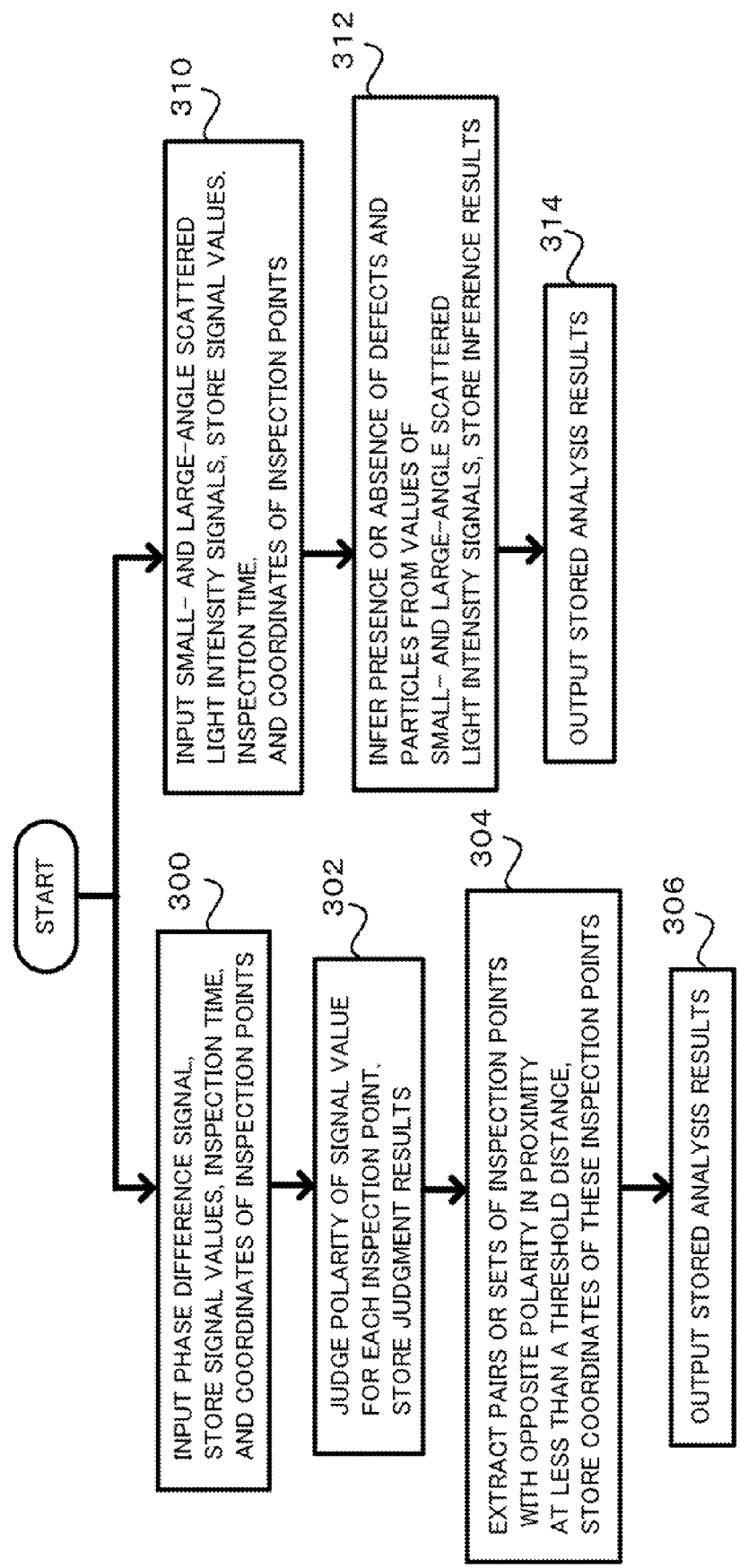

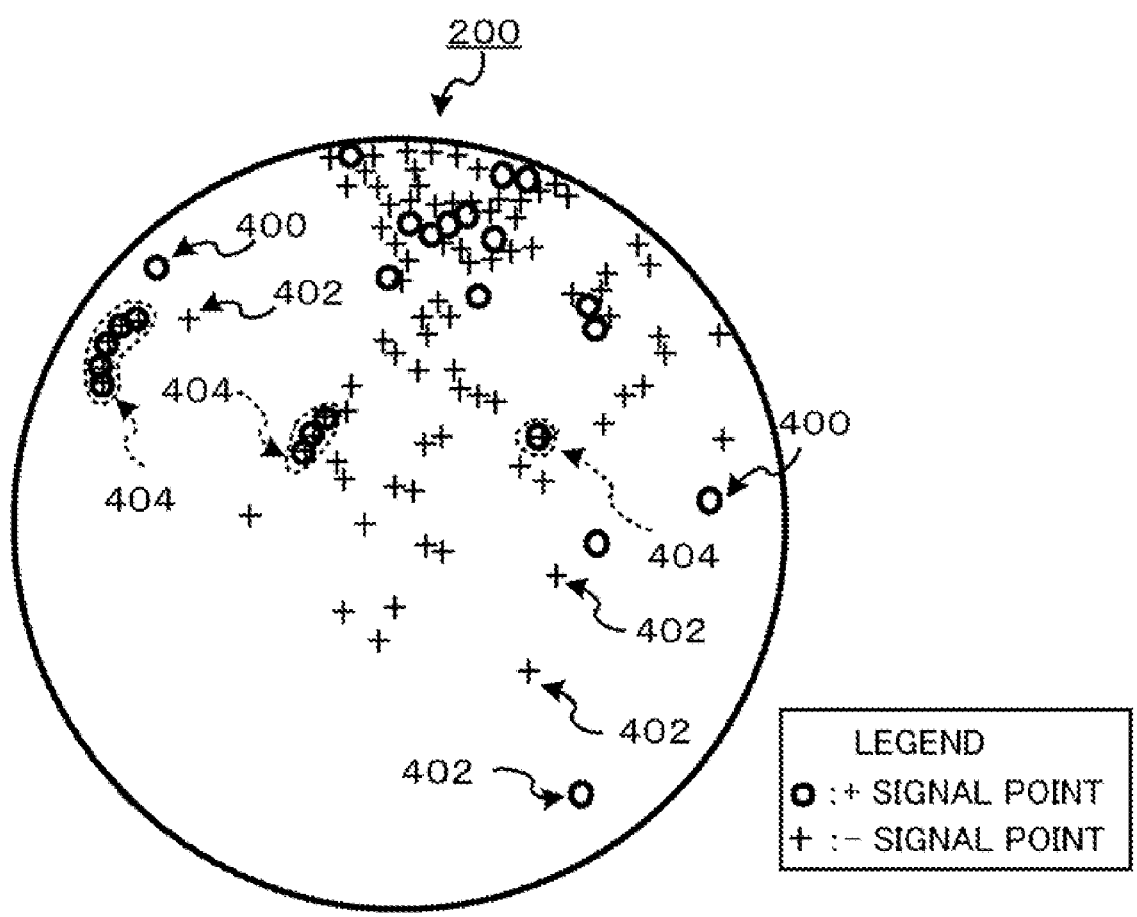

APPARATUS AND METHOD FOR INSPECTING SEMICONDUCTOR WAFER

TECHNICAL FIELD

The present invention relates to an apparatus and method for inspecting the surface stateL of semiconductor wafers, and in particular relates to an apparatus and method which are suitable for detection of LADs (Large Area Defects) on epitaxial wafers.

BACKGROUND ART

Among semiconductor wafer defects (structural or chemical abnormalities which detract from an ideal crystal structure in the surface layer of a semiconductor wafer), those defects which can be the cause of semiconductor device failure are called "killer defects". In the case of an epitaxial wafer, convex-shape SFs (Stacking Faults) and mounds have long been known as typical killer defects. Optical scattering methods are widely used as methods to detect such defects (see for example Japanese Patent Laid-open No. 2001-176943). According to the inspection method described in Japanese Patent Laid-open No. 2001-176943, a foreign matter inspection apparatus using an light scattering method (for example, KLA-Tencor's Surfscan 6200 (a registered trademark)) is used to irradiate the surface of the epitaxial wafer with a laser beam, the sizes of laser light scatterers existing on the wafer surface are measured, and laser light scatterers are judged to be stacking faults when their measured size exceed a prescribed value.

On the other hand, in recent years it has been found that broad flat defects the height of which is extremely low, ranging from several nanometers to several tens of nanometers, and the length-direction dimensions of which extend to several hundreds of microns, also rarely exist on the surface of epitaxial wafers. This type of defect is called a LAD (Large Area Defect). LADs are also "killer defects"; it has been reported that a LAD can result in defocus failures in semiconductor device manufacturing processes, and can cause degeneration of oxide film breakdown voltages and lifetimes.

While in general many of the killer defects other than LADs have heights of order ranging from several hundred nanometers to several hundred microns, the heights of LADs are, as explained above, extremely low, from nanometer order to several tens of nanometers. Because of these low heights, it is difficult to discover LADs using light scattering methods. And even when a LAD is discovered using a light scattering method, it is extremely difficult to differentiate a LAD from other laser light scatterers, such as for example particles or others defects on the wafer surface.

In Toshiya Sato et al, "Epitakisharu ueha ni okeru LAD no eikyou" (Effects of LADs on epitaxial wafers), pp. 35-40, Japan Soc. Applied Physics, Silicon Technology Division, No. 16, Apr. 24, 2000, it is reported that a foreign matter inspection apparatus using a light scattering method (for example, ADE's AWIS (a registered trademark)) can be used to differentiate LADs and particles (dust and other foreign matter on the wafer surface). According to this report, a laser beam is made obliquely incident on the wafer surface, P polarized light and S polarized light scattered from the surface are measured, and based on the intensities of both the P polarized light and the S polarized light, it is possible to judge whether a laser light scatterer on the wafer surface is a LAD or a particle.

In the method of Toshiya Sato et al, "Epitakisharu ueha ni okeru LAD no eikyou", pp. 35-40, Japan Soc. Applied Physics, Silicon Technology Division, No. 16, Apr. 24, 2000, scanning of the wafer surface must be repeated twice when measuring P polarized light and S polarized light, so that throughput is low. Moreover, when using this method, there is anticipated the further difficulty that, if the height or other parameters of a LAD are different, the judgment conditions applied to the intensities of the P polarized light and S polarized light must also be changed.

Hence an object of this invention is to enable detection of LADs on a semiconductor wafer and discrimate LADs from other laser light scatterers.

A further object is to enable detection of LADs on a semiconductor wafer in a single scanning operation.

DISCLOSURE OF THE INVENTION

A semiconductor wafer inspection apparatus according to one aspect of this invention comprises a scanning device, which irradiates each point of the surface of a semiconductor wafer with a laser beam while scanning the surface; a reflected-light sensor, which receives the laser beam reflected from each of the points irradiated with the laser beam, and outputs a signal; inclination point detection means, which receives the signal from the reflected-light sensor, and detects upward-inclination points having an inclination which rises in a prescribed direction and downward-inclination points having an inclination which falls; anomalous area detection means, which receives detection results from the inclination point detection means, and based on the positional relationship between the upward-inclination points and downward-inclination points, detects anomalous areas; and, output means, which output detection results from the anomalous area detection means.

In a preferred embodiment, the anomalous area detection means detects, as an anomalous area, an area in which both upward-inclination and downward-inclination points exist in proximity within a prescribed range of mutual distances.

In a preferred embodiment, the prescribed range of mutual distances is substantially 1000 μm or less.

In a preferred embodiment, the scanning device has an optical device which divides a signal source laser beam into two parallel laser beams, irradiates each of the points with the two laser beams, combines the two reflected laser beams from each of the points irradiated with the two irradiating laser beams, and generates a combined laser beam; the reflected-light sensor receives the combined laser beam and outputs a signal according to the phase difference between the two reflected laser beams; and, the inclination point detection means detects upward-inclination points and downward-inclination points by judging whether phase difference between the two reflected laser beams is positive or negative, based on the signal from the reflected-light sensor.

A preferred embodiment further comprises: a scattered-light sensor, which is operated simultaneously with the reflected-light sensor, and which receives scattered light from each of the points irradiated with the laser beam and outputs signal; anomalous location detection means, which receives the signal from the scattered-light sensor and detects an anomalous location based on the scattered light intensity; and means for outputting detection results from the anomalous location detection means.

A semiconductor wafer inspection method according to another aspect of this invention comprises a step of irradiating each point of the semiconductor wafer surface with a laser beam, while scanning the surface; a step of receiving the reflected laser beam from each point irradiated with the laser beam, and of detecting upward-inclination points having an upward inclination in a prescribed direction and downward-inclination points having a downward inclination; a step of receiving detection results from inclination point detection means, and detecting anomalous areas inferred to be LADs based on the positional relation between upward-inclination and downward-inclination points; and a step of outputting the detection results for the anomalous areas.

By means of this invention, LADs on a semiconductor wafer can be detected and discriminated from other laser light scatterers by a single operation of scanning the semiconductor laser surface.

BRIEF DESCRIPTION OF THE DRAWINGS

FIG. 3 shows the flow of analysis processing performed by a signal processing device; and, FIG. 4 shows an example of analysis results by a signal differential analyzer.

BEST MODE FOR CARRYING OUT THE INVENTION

Figure 1:
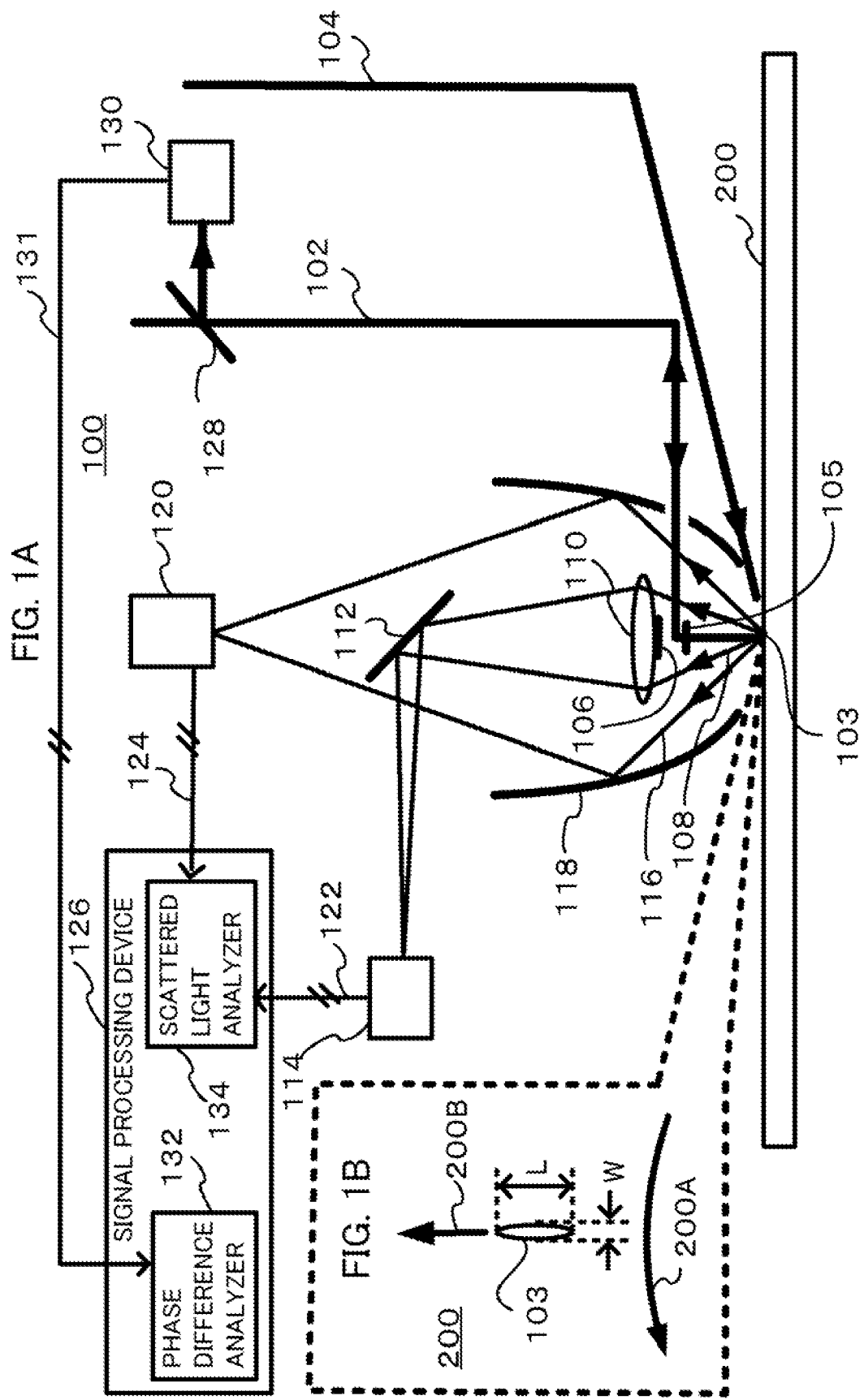
FIG. 1A is a cross-sectional side view showing the configuration of the semiconductor wafer inspection apparatus of an aspect of the invention.
FIG. 1B is a plane view showing the manner in which the surface of a semiconductor wafer is scanned by a light spot.
Figure 2:
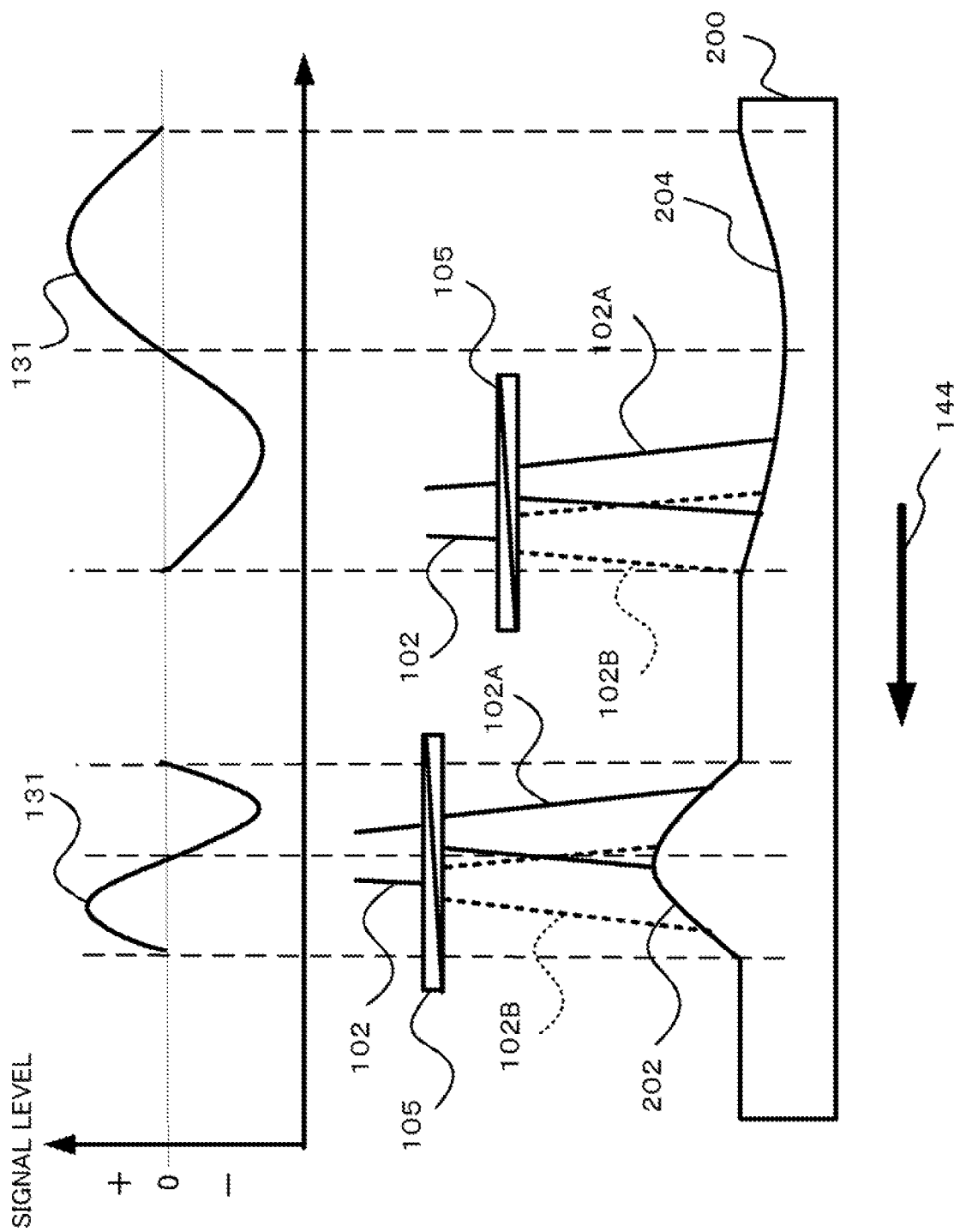
FIG. 2 shows the manner of irradiation of a semiconductor wafer surface with two parallel laser beams, as well as the relation between the shape of the semiconductor wafer surface and the level of the phase difference signal.

FIG. 1A is a cross-sectional side view showing the configuration of the semiconductor wafer inspection apparatus of an aspect of the invention. FIG. 1B is a plane view showing the manner in which the surface of a semiconductor wafer is scanned by a light spot. FIG. 2 is an enlarged view of laser beams irradiating the surface of a semiconductor wafer.

As shown in FIG. 1A, this inspection apparatus 100 can irradiate one point (an inspection point) on the surface of a semiconductor wafer 200 selectively with two types of laser beam 102, 104. One of the laser beams 102 is incident perpendicularly on the surface of the semiconductor wafer 200; the other laser beam 104 is incident at an oblique angle on the surface of the semiconductor wafer 200. In this aspect, only the perpendicularly-incident laser beam 102 is used, and the obliquely-incident laser beam 104 is not used.

FIG. 1B shows a laser spot 103 formed at the inspection point by the perpendicularly-incident laser beam 102. The diameter of the laser spot 103 (the thickness of the laser beam 102) is on the order from ten μm to several hundreds of μm. That is, the laser spot 103 has for example a long, thin elliptical shape, and the major-axis dimension L is for example several hundred μm (more specifically, for example, 340 μm), whereas the minor-axis dimension W is for example several tens of μm (more specifically, for example, 20 μm) in size. The major axis and minor axis of the laser spot 103 are directed in directions parallel to the radial line and the circumferential line of the semiconductor wafer 200 respectively. The inspection apparatus 100 rotates the semiconductor wafer 200 about the center point as indicated by the arrow 200A, and simultaneously moves the semiconductor wafer 200 along the radial line as indicated by the arrow 200B. By this means, the laser spot 103 scans the entire area of the surface of the semiconductor wafer 200 in a spiral shape. The interval between spiral-shape scan lines (the interval in the radial direction between the Nth rotation and the N+1th rotation scan lines) is approximately 20 μm, equal to the minor-axis dimension W of the laser spot 103.

As shown in FIG. 2, the perpendicularly-incident laser beam 102 is divided into two parallel laser beams 102A, 102B, arranged in the scanning direction, by a beam splitter 105, and these two laser beams 102A, 102B irradiate the inspection point on the semiconductor wafer 200. The size of the above-described laser beam spot 103 is the size of these two laser beams 102A, 102B combined.

Referring again to FIG. 1A, the perpendicularly-incident laser beam 102 is reflected in directions according to the surface shape of the inspection point on the semiconductor wafer 200. For example, when neither defects nor particles exist at the inspection point, the surface at the inspection point is perpendicular to the laser beam 102 and is flat, and so the laser beam 102 becomes a substantially perpendicular reflected laser beam, and returns on the same path as the path of incidence in the opposite direction. On the other hand, when a defect or a particle exists at the inspection point, the surface protrudes or is depressed, and a portion of the laser beam 102 becomes a perpendicular reflected laser beam, but other portions become scattered light 108, 116.

As previously explained using FIG. 2, the perpendicularly-incident laser beam 102 is divided into two parallel laser beams 102A, 102B which are incident on the inspection point. Hence the perpendicular reflected laser beam from the inspection point in fact comprises two reflected laser beams. These two perpendicular reflected laser beams are recombined by the beam splitter 105 to become a single combined reflected laser beam, which is input to the first optical sensor 130 by the half-mirror 128. The combined reflected laser beam has an intensity corresponding to the phase difference between the two reflected laser beams from the inspection point. The first optical sensor 130 receives the combined reflected laser beam, generates an electrical signal (for example, a voltage signal) (hereafter called a "phase difference signal") 131 having a level corresponding to the phase difference between the two reflected laser beams, and outputs this signal to the signal processing device 126.

On the other hand, the scattered reflected light 108, 116 from the inspection point is input to two scattered light sensors 114 and 120, according to the scattering angle (reflection angle). That is, light 108 which is scattered and reflected in a small angle range where the scattering angle is equal to or less than a prescribed value (for example, in the range of reflection angles from 6.5 degrees to 20 degrees) (hereafter called "small-angle scattered light") passes through a convex lens 110 and is reflected by a reflecting mirror 112, and is input to a second optical sensor 114. Light 116 which is scattered and reflected in a large angle range where the scattering angle is equal to or greater than a prescribed value (for example, in the range of reflection angles from 25 degrees to 70 degrees) (hereafter called "large-angle scattered light") is reflected by a solid concave reflecting mirror 118, and is input to a third optical sensor 120. The second optical sensor 114 generates electrical signal (for example, voltage signal) (hereafter called "small-angle scattered light intensity signal") 122 having levels according to the intensity of the small-angle scattered light 108, and outputs the signal to the signal processing device 126. The third optical sensor 120 generates electrical signal (for example, voltage signal) (hereafter called "large-angle scattered light intensity signal") 124 having levels according to the intensity of the large-angle scattered light 116, and outputs the signal to the signal processing device 126.

The signal processing device 126 has a phase difference analyzer 132 and a scattered light analyzer 134. The phase difference analyzer 132, by analyzing input phase difference signal 131, selectively detects LADs (large area flat defects, the height of which is extremely low at several nanometers to several tens of nanometers, and with a length-direction dimension on the order of several hundred μm or greater) on the surface of the semiconductor wafer 200, and stores and outputs the detection results. On the other hand, the scattered light analyzer 134, by analyzing small-angle scattered light intensity signal 122 and large-angle scattered light intensity signal 124, detects laser light scatterers (for example, stacking faults, mounds, particles and similar, with heights on the order of several hundred nanometers or greater) on the surface of the semiconductor wafer 200 (and in some cases may also detect LADs), discriminates the detected laser light scatterers as particles or as faults with a high probability of being a killer defect, and stores and outputs the discrimination results. The signal processing device 126 can for example be realized as a programmed computer, a hard-wired circuit, or as a combination of these.

FIG. 2 shows the relation between the above-described phase difference signal 131 and the surface shapes of inspection points.

As shown in FIG. 2, when the two parallel laser beams 102A, 102B are incident on a portion of the wafer having an inclination, a phase difference occurs between the reflected light of the two laser beams 102A, 102B, and the intensity of the combined reflected beam resulting by recombining these changes. The intensity change of the combined reflected beam appears in the level of the phase difference signal 131; as illustrated, when for example the inclination is upwards in the scanning direction, the phase difference signal 131 is positive, and when the inclination is downwards, the phase difference signal 131 is negative.

The resolution of the height of the inclination in the phase difference signal 131 depends on the wavelength of the laser beam, but may for example be approximately several nanometers. Because LAD heights are from several nanometers to several tens of nanometers, LAD detection is possible using phase difference signal 131 having a height resolution of approximately several nanometers. An area of a LAD is larger than the laser spot 103 in planar size, and within the area the upward inclinations and downward inclinations of the protrusions 202 and depressions 204 exist in proximity. Hence when the above-described two parallel laser beams 102A, 102B irradiate a LAD, the phase difference signal 131 become positive and negative at mutually proximate inspection points. On the other hand, most laser light scatterers other than LADs, such as stacking faults, mounds and particles, are higher than LADs in height, and smaller than the laser spot 103 in planar size. Hence when the two laser beams 102A, 102B irradiate a laser light scatterer other than a LAD, normally the phase difference signal 131 is positive only. Further, in regions in which the surface of the semiconductor wafer is slightly curved, and inclinations due to this slight curvature exist, phase difference signal 131 will be of only one kind, either positive or negative.

The phase difference analyzer 132 of the signal processing device 126 utilizes this principle to selectively detect LADs. That is, the phase difference analyzer 132 discovers an area where an inspection point at which the phase difference signal 131 is positive (that is, an inspection point at which an upward inclination exists) and another inspection point at which the phase difference signal 131 is negative (that is, an inspection point at which a downward inclination exists) exist in proximity within a prescribed range of mutual distances, and judges such an area to be a LAD. Here, in light of the general planar size of a LAD, as the above prescribed range of mutual distances can for example be set to the range of mutual distances of 1000 μm or less, or to a range of several hundred μm or less.

FIG. 3 shows the flow of processing performed by the signal processing device 126.

In FIG. 3, the routine from step 300 to step 306 is processing performed by the phase difference analyzer 132. The routine from step 310 to step 314 is processing performed by the scattered light analyzer 134. These two routines are performed simultaneously in parallel.

In step 300, while the surface of the semiconductor wafer 200 is being scanned by the two perpendicular-incident laser beams 102A, 102B, the phase difference analyzer 132 inputs phase difference signal 131 having values according to the phase difference in the two perpendicular reflected laser beams at each inspection point, and stores the value of the phase difference signal 131 together with the inspection time and the coordinates of each inspection point. Simultaneously with this, in step 310 the scattered light analyzer 134 takes as inputs the small-angle scattered light intensity signal 122 and large-angle scattered light intensity signal 124, having values according to the respective intensities of the small-angle scattered light 108 and large-angle scattered light 116 from each inspection point, and stores the values of these signals 122, 124 together with the inspection time and the coordinates of each inspection point.

In step 302, the phase difference analyzer 132 judges the polarity (positive or negative) of the phase difference signal value stored for each inspection point, and stores the judgment results. In step 304, the phase difference analyzer 132 detects, based on the polarities and coordinates of phase difference signal values stored for the inspection points, areas in each of which a pair or a set of inspection points having both positive and negative phase difference signal values exist in proximity within the range of the prescribed threshold of mutual distances, as anomalous areas, and stores the coordinates of the detected anomalous areas. Here, the detected anomalous areas are surmised to be LADs. In step 306, the above-described analysis results stored by the phase difference analyzer 132 are output to a display device, an external device, or similar.

In step 312, the scattered light analyzer 134 detects, based on the values of the small-angle scattered light intensity signal 122 and large-angle scattered light intensity signal 124 stored for each inspection point, whether a laser light scatterer such as a defect, particle, or the like exists at each inspection point, and whether the detected laser light scatterer is a defect or a particle, and stores the inference results. In step 314, the above analysis results stored by the scattered light analyzer 134 are output to a display device, external device, or similar. As the method of analysis performed by the scattered light analyzer 134 to discriminate between defects and particles based on the small-angle scattered light intensity signal 122 and large-angle scattered light intensity signal 124, a well-known method can be used.

In this way, by performing a single scan of the semiconductor wafer surface, the phase difference analyzer 132 detects anomalous areas surmised to be LADs, and simultaneously, the scattered light analyzer 134 detects anomalous locations in which defects or particles are inferred to exist.

FIG. 4 shows an example of analysis results by the phase difference analyzer 132.

In FIG. 4, circles denote inspection points 400 at which the phase difference signal is positive; + symbols denote inspection points 402 at which the phase difference signal is negative. As shown in FIG. 4, areas 404 in each of which a pair or a set of inspection points 400 and 402 having both positive and negative values of the phase difference signal exist in proximity within a prescribed range of mutual distance (in FIG. 4, due to the circumstances of the diagram, circles and + symbols substantially overlap at the same positional are detected as anomalous areas 404 which are inferred to be LADs.

In the above, an embodiment of this invention has been explained; but this embodiment is merely an example used in explaining the invention, and the scope of the invention is not limited only to this embodiment. This invention can be implemented in various other embodiments without deviating from the gist thereof.

The invention claimed is:

1. A semiconductor wafer inspection apparatus, comprising:
   a scanning device which irradiates each point of a surface of a semiconductor wafer (200) with a laser beam (102) while scanning said surface;
   a reflected-light sensor (130) which receives the laser beam reflected from each of said points irradiated with said laser beam (102), and outputs a signal (131);
   an inclination point detection means (132, 302), which receives the signal (131) from said reflected-light sensor (130), and detects upward-inclination points (400) having an inclination which rises in a prescribed direction and downward-inclination points (402) having an inclination which falls;
   anomalous area detection means (132, 304) which receives detection results from said inclination point detection means (132, 302), and based on positional relationship between said upward-inclination points and said downward-inclination points, detects anomalous areas (404); and
   output means (132, 306) which outputs detection results from the anomalous area detection means,
   wherein said anomalous area detection means (132, 304) detects, as said anomalous area, an area in which both said upward-inclination point (400) and said downward-inclination point (402) exist in proximity within a prescribed range of mutual distances.

2. The semiconductor wafer inspection apparatus according to claim 1, wherein said prescribed range of mutual distances is substantially 1000 μm or less.

3. A semiconductor wafer inspection method, comprising the steps of:
   (a) irradiating each point of a semiconductor wafer surface with a laser beam, while scanning said surface;
   (b) receiving the reflected laser beam from each of said points irradiated with said laser beam, and detecting upward-inclination points having an upward inclination in a prescribed direction and downward-inclination points having a downward inclination;
   (c) receiving detection results from inclination point detection means, and detecting anomalous areas based on positional relation between said upward-inclination points and said downward-inclination points; and
   (d) outputting the detection results for said anomalous areas
   wherein in step (c) an area in which both said upward-inclination points and said downward-inclination points exist in proximity within a prescribed range of mutual distances is detected as said anomalous area.

* * * * *

UNITED STATES PATENT AND TRADEMARK OFFICE
CERTIFICATE OF CORRECTION

PATENT NO.         : 7,522,290                                    Page 1 of 1
APPLICATION NO. : 11/569249
DATED              : April 21, 2009
INVENTOR(S)        : Fumi Nabeshima and Kazuya Togashi It is certified that error appears in the above-identified patent and that said Letters Patent is hereby corrected as shown below:

On the title page, item (73) the assignee name should read as follows:

--SUMCO TECHXIV CORPORATION,
  Nagasaki (JP)--

Signed and Sealed this

Seventh Day of July, 2009

JOHN DOLL
*Acting Director of the United States Patent and Trademark Office*